(12) United States Patent
Oh et al.

(10) Patent No.: US 11,301,518 B2
(45) Date of Patent: *Apr. 12, 2022

(54) SYSTEMS AND METHODS FOR SEARCHING AND INDEXING DOCUMENTS COMPRISING CHEMICAL INFORMATION

(71) Applicant: PerkinElmer Informatics, Inc., Waltham, MA (US)

(72) Inventors: Churl Oh, Concord, MA (US); David Gosalvez, Pembroke, MA (US); Pavel Khomiakov, Acton, MA (US)

(73) Assignee: PerkinElmer Informatics, Inc., Waltham, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 16/739,799

(22) Filed: Jan. 10, 2020

(65) Prior Publication Data

US 2020/0151221 A1 May 14, 2020

Related U.S. Application Data

(63) Continuation of application No. 15/474,865, filed on Mar. 30, 2017, now Pat. No. 10,572,545.

(Continued)

(51) Int. Cl.
*G06F 16/22* (2019.01)
*G06F 16/93* (2019.01)
(Continued)

(52) U.S. Cl.
CPC .............. *G06F 16/93* (2019.01); *G06F 16/22* (2019.01); *G06F 16/245* (2019.01);
(Continued)

(58) Field of Classification Search
CPC ........ G06F 16/93; G06F 16/22; G06F 16/245; G06F 16/2425; G06F 16/3334; G06F 16/248; G16C 20/90; G16C 20/40
(Continued)

(56) References Cited

U.S. PATENT DOCUMENTS 9,047,267 B2 6/2015 Xie et al.
2003/0023584 A1* 1/2003 Brandin ................. G06F 16/986
(Continued)

FOREIGN PATENT DOCUMENTS

JP 6215038 B2 10/2017
WO 0108032 A2 2/2001

OTHER PUBLICATIONS

Mar. 7, 2019—U.S. Non-final Office Action—U.S. Appl. No. 15/474,865.
(Continued)

*Primary Examiner* — Hanh B Thai
(74) *Attorney, Agent, or Firm* — Banner & Witcoff, Ltd.

(57) ABSTRACT

Described herein are systems and methods for indexing document data in order to facilitate chemical structure searching. The document data may include chemical structure data corresponding to a chemical structure. Bit-screening data and connection data in the chemical structure data may be identified. The bit-screening data may correspond to constituent elements of the chemical structure, and the connection data may correspond to connections between the one or more constituent elements. A string tag may be generated based on a portion of the identified bit-screening data. The string tag may include an alphanumeric value for describing the chemical structure that corresponds to the chemical structure data. The document data may be indexed based on the string tag. The chemical structure data corresponding to a chemical structure in the document may be
(Continued)

searchable based on correlating at least a portion of text data of a query with the indexed document data.

20 Claims, 10 Drawing Sheets

Related U.S. Application Data

(60) Provisional application No. 62/466,764, filed on Mar. 3, 2017.

(51) Int. Cl.
    *G06F 16/245*     (2019.01)
    *G06F 16/248*     (2019.01)
    *G06F 16/242*     (2019.01)
    *G16C 20/40*     (2019.01)
    *G06F 16/33*     (2019.01)
    *G16C 20/90*     (2019.01)
    *G16C 20/70*     (2019.01)

(52) U.S. Cl.
    CPC ........ *G06F 16/248* (2019.01); *G06F 16/2425* (2019.01); *G06F 16/3334* (2019.01); *G16C 20/40* (2019.02); *G16C 20/70* (2019.02); *G16C 20/90* (2019.02)

(58) Field of Classification Search
    USPC .......................................................... 707/722
    See application file for complete search history.

(56) References Cited

U.S. PATENT DOCUMENTS

| | | |
|---|---|---|
| 2004/0006559 A1 | 1/2004 | Gange et al. |
| 2005/0203898 A1 | 9/2005 | Boyer et al. |
| 2008/0021798 A1 | 1/2008 | Achten et al. |
| 2008/0059417 A1* | 3/2008 | Yamada .................. G06F 16/81 |
| 2008/0140616 A1 | 6/2008 | Encina et al. |
| 2009/0019015 A1* | 1/2009 | Hijikata ................. G06F 16/951 |
| 2010/0281030 A1* | 11/2010 | Kusumura ............ G06F 16/835 707/741 |
| 2011/0276589 A1 | 11/2011 | Smith et al. |
| 2012/0233185 A1 | 9/2012 | Najjar et al. |
| 2015/0121199 A1 | 4/2015 | Wu et al. |
| 2016/0299888 A1 | 10/2016 | Wu et al. |
| 2017/0344548 A1* | 11/2017 | Tietjen ................. G06F 16/2255 |

OTHER PUBLICATIONS

Sep. 18, 2019—U.S. Notice of Allowance—U.S. Appl. No. 15/474,865.
Jan. 20, 2021—(CA) Office Action—App. No. 3,055,172.
Sep. 9, 2020—(EP) Office Action—App 17716427.4.
Oct. 25, 2017—(PCT) U.S. Written Opinion and International Search Report—App 2017/025126.
Klekota, J., Roth, F.P, and Schreiber, S.L., "Query Chem: a Google-powered web search combining text and chemical structures", Bioinformatics, vol. 22, No. 13, May 3, 2006, pp. 1670-1673.
Tönnies, S, Köhncke, B., and Balke, W-T, "Taking Chemistry to the Task—Personalized Queries for Chemical Digital Libraries," Jun. 13, 2011, pp. 325-334.
Various authors: "Chemical Database—Wikipedia", Wikipedia online encyclopedia, Aug. 1, 2016 (retrieve from "https://en.wikipedia org/w/index.php?title=Chemical_database&oldid=732531151"—6 pages.
Dec. 22, 2020—(JP) Office Action—App. No. 2019-569655.
Yumiko Tomikawa et al., "Nikkaji Web Has Been Released", Journal of Information Processing and Management, Japan Science and Technology Agency, Jul. 1, 2005, vol. 48, No. 4, p. 220-225.
Oct. 5, 2021 (IN) First Examination Report—App. No. 201947038234.
Klekota, Justin et al., "Query Chem: a Google-Powered Web Search Combining Text and Chemical Structures," Oxford University Press, vol. 22, No. 13, 2006, pp. 1670-1673.
Tonnies, Sascha et al., "Taking Chemistry to the Task—Personalized Queries for Chemical Digital Libraries," JCDL, Jun. 13-17, 2011.
Jan. 20, 2022 (EP) Summons to Attend Oral Proceedings—App. No. 17716427.4.

\* cited by examiner

SYSTEMS AND METHODS FOR SEARCHING AND INDEXING DOCUMENTS COMPRISING CHEMICAL INFORMATION

RELATED APPLICATIONS

This application claims priority to U.S. patent application Ser. No. 15/474,865 filed Mar. 30, 2017, which claims priority to U.S. Provisional Application 62/466,764 filed Mar. 3, 2017, the entire disclosure of which is hereby incorporated herein by reference.

FIELD OF INVENTION

This invention relates generally to systems and methods for efficiently searching and indexing documents comprising chemical information.

BACKGROUND

Chemical structures are typically represented in documents using graphical notations to provide a reader with a more complete understanding of relevant chemical information. For example, a chemical structure may be drawn using a representation such as a Lewis structure, skeletal formula, Newman projection, sawhorse projection, or Fischer projection, amongst others. A chemical structure may also be represented by a condensed formula that omits certain commonly understood constituent elements (e.g., bonds or terminal hydrogens) to simplify the overall representation of the structure. Graphical representations of chemical structures may be presented in documents in various contexts, for example, to illustrate the roles of corresponding chemicals in a chemical reaction, to describe a reaction product, or to provide a comparison between structurally similar, but chemically distinct entities. Frequently, the graphical representation of a chemical structure represents the key information in a document that identifies the chemical as relevant to a user for a particular desired purpose.

In order to reproduce chemical structures in a document, a range of standard formats are used to efficiently store the chemical structure data. One type of format uses connection tables, adjacency matrices, or similar data structures to relate atoms and bonds as edges and nodes. Another type of format uses linear string notations based on depth first or breadth first traversal. The use of standardized data formats for storing chemical structure data enables algorithmic searching of the data. Furthermore, chemical structure data in standard formats can be indexed with a document in a database.

A user will commonly perform a search of a database of documents to identify documents that refer to one or more relevant chemical structures. The user must enter an input that is capable of being compared to the chemical structures stored in the database of documents. The user may enter a query by providing chemical structure data or a characteristic name, such as one according to the International Union of Pure and Applied Chemistry (IUPAC) conventions. The user-provided input is converted to a standard format used to store chemical structure data in the database and compared against chemical structure data contained within indexed documents using a variety of techniques.

Generally, documents in a database responsive to a user's search are identified by determining similarity between chemical structures in the documents and the user provided input using graph-theory-based algorithmic approaches. Frequently, similarity is established by determining whether fragments (e.g., constituent elements) of the user-provided input structure are present in chemical structures in the documents. This may be done, for example, using a binary fingerprint of the chemical structure. If a sufficient number or proportion of fragments identified in the user's input are present in a chemical structure in a document, then similarity is established. The similarity may be used to screen out unrelated documents before searching the chemical structures in unscreened documents using an atom-by-atom comparison to establish the search results provided to the user. Alternatively, all documents containing chemical structures whose similarity to the search input exceeds a threshold may be provided as search results to the user.

Various algorithms have modified this basic approach of establishing similarity in order to accelerate search speed, such as the class of algorithms using hashed fingerprints. Accelerated search methods are necessary for efficiently searching for large molecules and/or searching in large datasets. When a database contains a very large number of documents comprising chemical structures, searching for relevant documents is cumbersome, as each chemical structure in every document must be searched against for similarity to the input structure. Such searches are slow and resource-intensive.

A user may only be interested in a subset of all possibly relevant documents based on some criteria other than the chemical structure alone. For example, the user may be interested in chemical structures related to input structures that have certain desirable properties, that may be synthesized with certain yields, or that exhibit certain reactivities. These additional search limitations are most conveniently provided by the user as text that may be used to search any text data in documents of a particular database. In order to search for both the user's input chemical structure and any additionally-provided text, one search for the chemical structure and one search for the text must be run sequentially.

The use of sequential searching does not significantly accelerate the searching of very large databases. A standard chemical structure search may be performed first to establish a set of potentially relevant documents based on the chemical structure input followed by a search of that set for documents containing the text search terms. However, this approach may be no faster than a search that does not contain any additional text terms. Performing a search for documents containing user input text terms first will quickly eliminate some documents from the set of potentially relevant documents. However, many search terms a user may input will not significantly reduce the number of potentially relevant documents so as to significantly accelerate the speed of the search. For example, if a user is searching for documents with related structures where reaction yields are over 90%, the set of documents where reaction yields are over 90% will still include a very large number of documents with unrelated chemical structures.

There is a need for systems and methods to more efficiently search large databases of documents referring to chemicals based on user-provided input. Additionally, there is a need for systems and methods to index a database of documents referring to chemicals for more efficient searching.

SUMMARY

Described herein are systems and methods that efficiently search for documents related to chemical structures of interest to a user. In certain embodiments, text data and chemical structure data provided in a user query are simultaneously searched with a text-based search method to efficiently produce search results. Subsequent structure-based searching on the results of the text-based search produces precise results for a particular user query. This approach increases the speed of the structure-based search by reducing the amount of data the structure-based search searches over. Additionally described herein are systems and methods for indexing document data in order to facilitate this efficient searching.

Searching chemical structure data (e.g., in a document's data or a user query) using structure-based searching methods is time and resource intensive, while text-based search methods are comparatively fast. In order to search chemical structure data using text-based search methods, the chemical structure data must be augmented or converted to text data (e.g., a string). String tags can be used that identify, classify, and/or describe the chemical structure or any of its constituent elements corresponding to the chemical structure data. By generating string tags for chemical structure data, chemical structure data can be searched over and/or searched with using a fast text-based method. Thus, during indexing, chemical structure data in document data is augmented to include string tags for use in subsequent text-based searches. User queries consisting of or comprising chemical structure data can be augmented to comprise string tags to enable text-based searching with the user query.

In a database of indexed document data augmented with string tags based on chemical structure data therein, the chemical structure data and text data of the indexed document data may be simultaneously searched. A user may provide a query that consists of both chemical structure data and text data. Fast and efficient text-based search methods may be employed to perform the simultaneous search in order to identify a set of documents that are relevant to the user query. Text-based search methods may be used to search chemical structure data where chemical structure data are identified by their associated string tags. Simultaneously searching chemical structures and text using text-based methods narrows the set of potentially relevant documents efficiently by simultaneously excluding documents that contain neither the chemical structure data nor text data of a user query. The set of relevant documents resulting from the text-based search may be provided to the user for further use.

In certain embodiments, a structure-based search of the chemical structure data in the relevant document data resulting from the text-based search may be performed to further refine the search results before providing them to the user. The structure-based search may use any structure-based method to search the relevant chemical structure data. In certain embodiments, the structure-based search is an atom-by-atom search method. The structure-based search refines the set of documents resulting from the text-based search to include only documents related to chemical structures that meet a threshold of similarity to the chemical structure input by the user. The refined search results may be provided to the user for viewing. By first employing a text-based search that simultaneously searches text data and chemical structure data, the structure-based search is performed on a smaller amount of document data in the database, thus improving efficiency.

In one aspect, the present invention is directed to a method for searching a set of documents comprising chemical information, the method comprising the steps of: (a) receiving, by a processor of a computing device, a user query comprising user-input chemical structure data and text data (e.g., alphanumeric data), wherein the text data and the user-input chemical structure data correspond to at least one chemical structure; (b) identifying or extracting, by the processor, bit-screening data and connection data from the user-input chemical structure data, wherein the bit-screening data correspond to one or more constituent elements of the at least one chemical structure, and the connection data correspond to one or more connections (e.g., interactions, bonds) between a plurality of the one or more constituent elements; (c) augmenting, by the processor, the user query by generating one or more string tags based on at least a portion of the bit-screening data, such that the augmented user query comprises the one or more string tags, wherein the one or more string tags comprise a sequence of alphanumeric characters for describing the at least one chemical structure; (d) querying, using a text-based search method, by the processor, a database comprising document data corresponding to the set of documents, wherein querying comprises correlating at least a portion of the augmented user query with the document data to generate one or more text-based search results; and (e) optionally, outputting, by the processor, the one or more text-based search results.

In certain embodiments, the method comprises converting, by the processor, the bit-screening data and the connection data to one or more strings. In certain embodiments, the method further comprises the steps of: (f) searching, using a structure-based search method, subsequent to the querying step, by the processor, the one or more text-based search results by correlating at least a portion of the user-input chemical structure data with relevant chemical structure data of the one or more text-based search results to generate one or more refined search results, wherein the one or more text-based search results correspond to filtered document data comprising the relevant chemical structure data; and (g) outputting, by the processor, (e.g., rendering for display, or outputting to another processor for rendering for display) the one or more refined search results. In certain embodiments, the structure-based search method uses string data as input (e.g., is performed using a text search engine). In certain embodiments, the structure-based search comprises an atom by atom search.

In certain embodiments, at least one of the one or more string tags comprises natural language text.

In certain embodiments, the querying step (d) comprises generating, by the processor, the one or more text-based search results using a relevance search. In certain embodiments, the relevance search is a hit-scoring search.

In certain embodiments, step (f) comprises: combining, by the processor, the relevant chemical structure data of the one or more text-based search results into a minimum spanning tree; storing, by the processor, the minimum spanning tree on a non-transitory computer readable medium; and searching, by the processor, the minimum spanning tree.

In certain embodiments, the user-input chemical structure data correspond to a substructure or complete structure of the at least one chemical structure.

In certain embodiments, the document data corresponding to the set of documents have been augmented to comprise one or more indexing string tags. In certain embodiments, the querying step comprises correlating the at least a portion of the augmented user query with at least one of the one or more indexing string tags.

In another aspect, the present invention is directed to a method for searching a set of documents comprising chemical information, the method comprising the steps of: (a) receiving, by a processor of a computing device, a user query comprising user-input chemical structure data (e.g., binary data), wherein the user-input chemical structure data correspond to at least one chemical structure; (b) identifying or extracting, by the processor, bit-screening data and connection data from the user-input chemical structure data, wherein the bit-screening data correspond to one or more constituent elements of the at least one chemical structure, and the connection data correspond to one or more connections (e.g., interactions, bonds) between a plurality of the one or more constituent elements; (c) augmenting, by the processor, the user query by generating one or more string tags based on at least a portion of the bit-screening data and, optionally, generating one or more encoded strings based on at least a portion of the connection data, such that the augmented user query comprises the one or more string tags, wherein the one or more string tags comprise a sequence of alphanumeric characters for describing the at least one chemical structure; (d) querying, using a text-based search method, by the processor, a database comprising document data corresponding to the set of documents, wherein querying comprises correlating at least a portion of the augmented user query with the document data to generate one or more text-based search results; and (e) optionally, outputting, by the processor, the one or more text-based search results. In certain embodiments, the method further comprises the step of: converting, by the processor, the bit-screening data and the connection data to one or more strings.

In certain embodiments, the method further comprises the steps of: (f) searching, using a structure-based search method, subsequent to the querying step, by the processor, the one or more text-based search results by correlating at least a portion of the user-input chemical structure data with relevant chemical structure data of the one or more text-based search results to generate one or more refined search results, wherein the one or more text-based search results correspond to filtered document data comprising the relevant chemical structure data; and (g) outputting, by the processor, (e.g., rendering for display, or outputting to another processor for rendering for display) the one or more refined search results.

In certain embodiments, the structure-based search method uses string data as input (e.g., is performed using a text search engine). In certain embodiments, at least one of the one or more string tags comprises natural language text. In certain embodiments, the structure-based search comprises an atom by atom search.

In certain embodiments, the querying step (d) comprises generating, by the processor, the one or more text-based search results using a relevance search. In certain embodiments, the relevance search is a hit-scoring search.

In certain embodiments, step (f) comprises: combining, by the processor, the relevant chemical structure data of the one or more text-based search results into a minimum spanning tree; storing, by the processor, the minimum spanning tree on a non-transitory computer readable medium; and searching, by the processor, the minimum spanning tree.

In certain embodiments, the user-input chemical structure data correspond to a substructure or complete structure of the at least one chemical structure.

In certain embodiments, the document data corresponding to the set of documents have been augmented to comprise one or more indexing string tags. In certain embodiments, the querying step comprises correlating the at least a portion of the augmented user query with at least one of the one or more indexing string tags.

In another aspect, the present invention is directed to a method for text-based searching a set of indexed documents comprising chemical information, the method comprising the steps of: (a) receiving, by a processor of a computing device, a user query comprising text data (e.g., alphanumeric data), wherein the text data comprise a sequence of alphanumeric characters that describe at least one chemical structure; (b) querying, using a text-based search method, by the processor, a database comprising document data corresponding to the set of indexed documents, the document data having been augmented to include one or more index string tags, wherein querying comprises correlating at least a portion of the text data of the user query with the one or more index string tags to generate one or more text-based search results, wherein the one or more index string tags comprise a sequence of alphanumeric characters for describing the at least one chemical structure; and (c) outputting, by the processor, (e.g., rendering for display, or outputting to another processor for rendering for display) the one or more text-based search results. In certain embodiments, the one or more index string tags comprise natural language text.

In certain embodiments, the querying step comprises generating, by the processor, the one or more text-based search results using a relevance search. In certain embodiments, the relevance search is a hit-scoring search.

In another aspect, the present invention is directed to a method for indexing a document to facilitate chemical structure searching, the method comprising the steps of: receiving, by a processor of a computing device, document data corresponding to the document, wherein the document data comprise chemical structure data corresponding to a chemical structure; identifying or extracting, by the processor, bit-screening data and connection data in the chemical structure data, wherein the bit-screening data correspond to one or more constituent elements of the chemical structure, and the connection data correspond to connections (e.g., interactions, bonds) between the one or more constituent elements; generating, by the processor, a string tag based on at least a portion of the identified bit-screening data, the string tag comprising an alphanumeric value for describing the chemical structure that corresponds to the chemical structure data (e.g., for use in querying for documents comprising the chemical structure data); optionally, generating, by the processor, an encoded string based on at least a portion of the connection data; associating, by the processor, the string tag with the chemical structure data or the document data; and outputting, by the processor, the string tag (e.g., for storage on a non-transitory computer readable medium). In certain embodiments, the method comprises the step of: converting, by the processor, the bit-screening data and the connection data to one or more strings. In certain embodiments, the string tag comprises natural language text.

In certain embodiments, the method comprises the step of augmenting, by the processor, the document data, wherein the augmented document data comprise the string tag. In certain embodiments, the method comprises the step of storing, by the processor, the string tag on a second non-transitory computer readable medium. In certain embodiments, the method comprises indexing the string tag.

In certain embodiments, the document data comprise metadata. In certain embodiments, the metadata comprise a unique ID and a bucket ID (e.g., wherein the bucket ID is used to identify tenant in a multi-tenant system). In certain embodiments, the method comprises the step of: persisting, by the processor, the metadata (e.g., during the method for indexing the document).

In certain embodiments, the method comprises converting the connection data to one or more encoded strings. In certain embodiments, the connection data is stored, but not indexed.

In another aspect, the present invention is directed to a method for searching a set of indexed documents comprising chemical information using sequential searches, the method comprising the steps of: (a) receiving, by a processor of a computing device, a user query comprising user-input chemical structure data and text data; (b) querying, using a text-based search method, by the processor, a database comprising document data corresponding to the set of indexed documents, wherein querying comprises correlating at least a portion of the user-input chemical structure data with the document data (e.g., by augmenting or converting the chemical structure data prior to correlating with the document data) and at least a portion of the text data of the user query with the document data to generate filtered document data; (c) searching, using a structure-based search method, subsequent to the querying step, by the processor, the filtered document data, wherein searching comprises correlating at least a portion of user-input chemical structure data with relevant filtered chemical structure data in the filtered document data to generate one or more search results; and (d) outputting, by the processor, (e.g., rendering for display, or outputting to another processor for rendering for display) the one or more search results. In certain embodiments, the method comprises the step of: converting, by the processor, the chemical structure data to one or more strings.

In certain embodiments, the structure-based search method uses string data as input (e.g., is performed using a text search engine).

In certain embodiments, the method comprises the step of: augmenting, prior to step (b), by the processor, the user query by generating one or more string tags such that the augmented user query comprises the one or more string tags, wherein the one or more query string tags describe a chemical structure. In certain embodiments, step (b) comprises correlating at least one of the one or more string tags with the document data.

In certain embodiments, the document data comprise one or more index string tags. In certain embodiments, step (b) comprises correlating at least a portion of the text data with the one or more index string tags.

In another aspect, the present invention is directed to a system for searching a set of documents comprising chemical information, the system comprising: a processor; and a non-transitory computer readable medium having instructions stored thereon, wherein the instructions, when executed by the processor, cause the processor to: (a) receive, by the processor, a user query comprising user-input chemical structure data and text data (e.g., alphanumeric data), wherein the text data and the user-input chemical structure data correspond to at least one chemical structure; (b) identify, by the processor, bit-screening data and connection data from the user-input chemical structure data, wherein the bit-screening data correspond to one or more constituent elements of the at least one chemical structure, and the connection data correspond to one or more connections (e.g., interactions, bonds) between a plurality of the one or more constituent elements; (c) augment, by the processor, the user query by generating one or more string tags based on at least a portion of the bit-screening data, such that the augmented user query comprises the one or more string tags, wherein the one or more string tags comprise a sequence of alphanumeric characters for describing the at least one chemical structure; (d) query, using a text-based search method, by the processor, a database comprising document data corresponding to the set of documents, wherein querying comprises correlating at least a portion of the augmented user query with the document data to generate one or more text-based search results; and (e) optionally, output, by the processor, the one or more text-based search results. In certain embodiments, the instructions, when executed by the processor, cause the processor to: convert, by the processor, the bit-screening data and the connection data to one or more strings.

In certain embodiments, the instructions, when executed by the processor, further cause the processor to: (f) search, using a structure-based search method, subsequent to the querying step, by the processor, the one or more text-based search results by correlating at least a portion of the user-input chemical structure data with relevant chemical structure data of the one or more text-based search results to generate one or more refined search results, wherein the one or more text-based search results correspond to filtered document data comprising the relevant chemical structure data; and (g) output, by the processor, (e.g., rendering for display, or outputting to another processor for rendering for display) the one or more refined search results.

In certain embodiments, the structure-based search method uses string data as input (e.g., is performed using a text search engine). In certain embodiments, at least one of the one or more string tags comprises natural language text.

In certain embodiments, the structure-based search comprises an atom by atom search. In certain embodiments, the instructions, when executed by the processor, cause the processor to generate, by the processor, the one or more text-based search results using a relevance search. In certain embodiments, the relevance search is a hit-scoring search.

In certain embodiments, the instructions, when executed by the processor, cause the processor to: combine, by the processor, the relevant chemical structure data of the one or more text-based search results into a minimum spanning tree; store, by the processor, the minimum spanning tree on a non-transitory computer readable medium; and search, by the processor, the minimum spanning tree.

In certain embodiments, the user-input chemical structure data correspond to a substructure or complete structure of the at least one chemical structure.

In certain embodiments, the document data corresponding to the set of documents have been augmented to comprise one or more indexing string tags. In certain embodiments, the querying step comprises instructions to correlate, by the processor, the at least a portion of the augmented user query with at least one of the one or more indexing string tags.

In another aspect, the present invention is directed to a system for searching a set of documents comprising chemical information, the system comprising: a processor; and a non-transitory computer readable medium having instructions stored thereon, wherein the instructions, when executed by the processor, cause the processor to: (a) receive, by the processor, a user query comprising user-input chemical structure data (e.g., binary data), wherein the user-input chemical structure data correspond to at least one chemical structure; (b) identify or extract, by the processor, bit-screening data and connection data from the user-input chemical structure data, wherein the bit-screening data correspond to one or more constituent elements of the at least one chemical structure, and the connection data correspond to one or more connections (e.g., interactions, bonds) between a plurality of the one or more constituent elements; (c) augment, by the processor, the user query by generating one or more string tags based on at least a portion of the bit-screening data and, optionally, generating one or more encoded strings based on at least a portion of the connection data, such that the augmented user query comprises the one or more string tags, wherein the one or more string tags comprise a sequence of alphanumeric characters for describing the at least one chemical structure; (d) query, using a text-based search method, by the processor, a database comprising document data corresponding to the set of documents, wherein querying comprises correlating at least a portion of the augmented user query with the document data to generate one or more text-based search results; and (e) optionally, output, by the processor, the one or more text-based search results. In certain embodiments, the instructions, when executed by the processor, cause the processor to: convert, by the processor, the bit-screening data and the connection data to one or more strings.

In certain embodiments, the instructions, when executed by the processor, cause the processor to: (f) search, using a structure-based search method, subsequent to the querying step, by the processor, the one or more text-based search results by correlating at least a portion of the user-input chemical structure data with relevant chemical structure data of the one or more text-based search results to generate one or more refined search results, wherein the one or more text-based search results correspond to filtered document data comprising the relevant chemical structure data; and (g) output, by the processor, (e.g., rendering for display, or outputting to another processor for rendering for display) the one or more refined search results. In certain embodiments, the structure-based search method uses string data as input (e.g., is performed using a text search engine). In certain embodiments, at least one of the one or more string tags comprises natural language text. In certain embodiments, the structure-based search comprises an atom by atom search.

In certain embodiments, the instructions, when executed by the processor, cause the processor to generate, by the processor, the one or more text-based search results using a relevance search. In certain embodiments, the relevance search is a hit-scoring search.

In certain embodiments, the instructions, when executed by the processor, cause the processor to: combine, by the processor, the relevant chemical structure data of the one or more text-based search results into a minimum spanning tree; store, by the processor, the minimum spanning tree on a non-transitory computer readable medium; and search, by the processor, the minimum spanning tree.

In certain embodiments, the user-input chemical structure data correspond to a substructure or complete structure of the at least one chemical structure.

In certain embodiments, the document data corresponding to the set of documents have been augmented to comprise one or more indexing string tags. In certain embodiments, the querying step comprises instructions to correlate, by the processor, the at least a portion of the augmented user query with at least one of the one or more indexing string tags.

In another aspect, the present invention is directed to a system for text-based searching a set of indexed documents comprising chemical information, the system comprising: a processor; and a non-transitory computer readable medium having instructions stored thereon, wherein the instructions, when executed by the processor, cause the processor to: (a) receive, by the processor, a user query comprising text data (e.g., alphanumeric data), wherein the text data comprise a sequence of alphanumeric characters that describe at least one chemical structure; (b) query, using a text-based search method, by the processor, a database comprising document data corresponding to the set of indexed documents, the document data having been augmented to include one or more index string tags, wherein querying comprises correlating at least a portion of the text data of the user query with the one or more index string tags to generate one or more text-based search results, wherein the one or more index string tags comprise a sequence of alphanumeric characters for describing the at least one chemical structure; and (c) output, by the processor, (e.g., rendering for display, or outputting to another processor for rendering for display) the one or more text-based search results. In certain embodiments, the one or more index string tags comprise natural language text.

In certain embodiments, the querying step comprises instructions to generate, by the processor, the one or more text-based search results using a relevance search. In certain embodiments, the relevance search is a hit-scoring search.

In another aspect, the present invention is directed to a system for indexing a document to facilitate chemical structure searching, the system comprising: a processor; and a non-transitory computer readable medium having instructions stored thereon, wherein the instructions, when executed by the processor, cause the processor to: receive, by a processor of a computing device, document data corresponding to the document, wherein the document data comprise chemical structure data corresponding to a chemical structure; identify or extract, by the processor, bit-screening data and connection data in the chemical structure data, wherein the bit-screening data correspond to one or more constituent elements of the chemical structure, and the connection data correspond to connections (e.g., interactions, bonds) between the one or more constituent elements; generate, by the processor, a string tag based on at least a portion of the identified bit-screening data, the string tag comprising an alphanumeric value for describing the chemical structure that corresponds to the chemical structure data (e.g., for use in querying for documents comprising the chemical structure data); associate, by the processor, the string tag with the chemical structure data or the document data; and output, by the processor, the string tag (e.g., for storage on a non-transitory computer readable medium). In certain embodiments, the instructions, when executed by the processor, cause the processor to: convert, by the processor, the bit-screening data and the connection data to one or more strings. In certain embodiments, the string tag comprises natural language text.

In certain embodiments, the instructions, when executed by the processor, cause the processor to: augment, by the processor, the document data, wherein the augmented document data comprise the string tag. In certain embodiments, the instructions, when executed by the processor, cause the processor to: store, by the processor, the string tag on a second non-transitory computer readable medium. In certain embodiments, the instructions, when executed by the processor, cause the processor to index the string tag.

In certain embodiments, the document data comprise metadata. In certain embodiments, the metadata comprise a unique ID and a bucket ID (e.g., wherein the bucket ID is used to identify tenant in a multi-tenant system). In certain embodiments, the instructions, when executed by the processor, cause the processor to: persist, by the processor, the metadata (e.g., while indexing the document).

In certain embodiments, the instructions, when executed by the processor, cause the processor to convert the connection data to one or more encoded strings. In certain embodiments, the instructions, when executed by the processor, cause the processor to store, but not index, the connection data.

In another aspect, the present invention is directed to a system for searching a set of indexed documents comprising chemical information using sequential searches, the system comprising: a processor; and a non-transitory computer readable medium having instructions stored thereon, wherein the instructions, when executed by the processor, cause the processor to: (a) receive, by the processor, a user query comprising user-input chemical structure data and text data; (b) query, using a text-based search method, by the processor, a database comprising document data corresponding to the set of indexed documents, wherein querying comprises correlating at least a portion of the user-input chemical structure data with the document data (e.g., by augmenting or converting the chemical structure data prior to correlating with the document data) and at least a portion of the text data of the user query with the document data to generate filtered document data; (c) search, using a structure-based search method, subsequent to the querying step, by the processor, the filtered document data, wherein searching comprises correlating at least a portion of user-input chemical structure data with relevant filtered chemical structure data in the filtered document data to generate one or more search results; and (d) output, by the processor, (e.g., rendering for display, or outputting to another processor for rendering for display) the one or more search results. In certain embodiments, the instructions, when executed by the processor, cause the processor to: convert, by the processor, the chemical structure data to one or more strings. In certain embodiments, the structure-based search method uses string data as input (e.g., is performed using a text search engine).

In certain embodiments, the instructions, when executed by the processor, cause the processor to: augment, prior to step (b), by the processor, the user query by generating one or more string tags such that the augmented user query comprises the one or more string tags, wherein the one or more query string tags describe a chemical structure. In certain embodiments, the instructions, when executed by the processor, cause the processor to: correlate, by the processor, at least one of the one or more string tags with the document data.

In certain embodiments, the document data comprise one or more index string tags. In certain embodiments, the instructions, when executed by the processor, cause the processor to correlate, by the processor, at least a portion of the text data with the one or more index string tags.

BRIEF DESCRIPTION OF THE DRAWINGS

Drawings are presented herein for illustration purposes, not for limitation. The foregoing and other objects, aspects, features, and advantages of the invention will become more apparent and may be better understood by referring to the following description taken in conjunction with the accompanying drawings, in which.

DEFINITIONS

Figure 1:
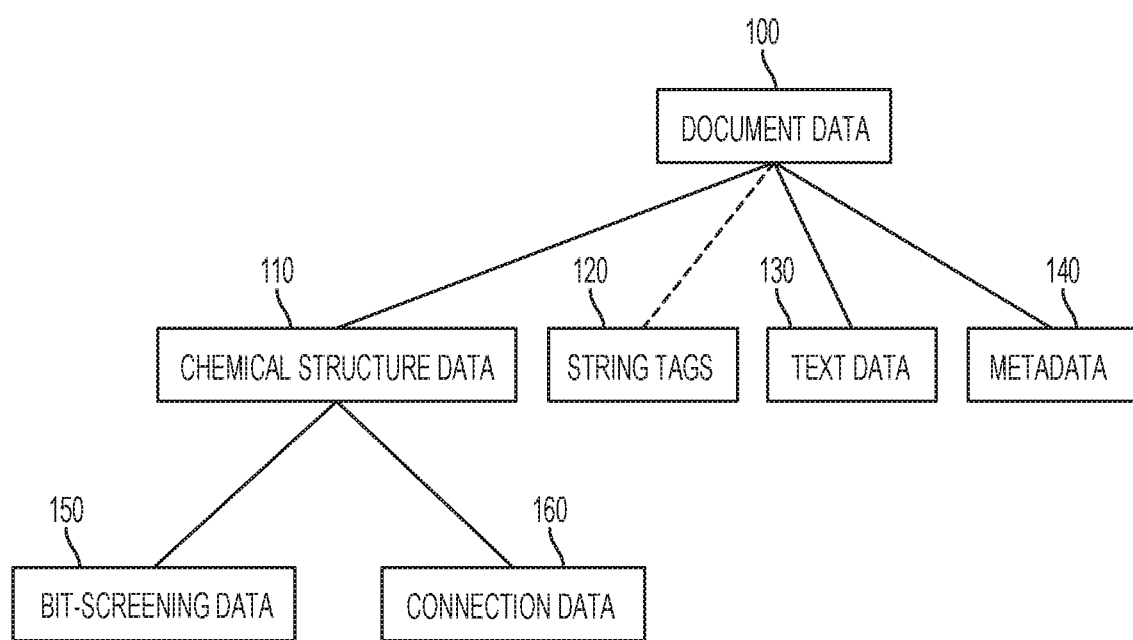
FIG. 1 shows a hierarchy of data structures corresponding to a document comprising chemical information, according to an illustrative embodiment of the present invention.

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Constituent element: As used herein, the phrase "constituent element" refers to a portion of a chemical structure. A constituent element may be a bond, an atom, a fragment, a functional group, a heteroatom, a moiety or any combination thereof that forms in whole or in part a chemical structure. A constituent element may be used to identify, describe, and/or classify a chemical structure. A constituent element may be used as a search term when querying for documents related to a chemical structure that comprises the constituent element.

Document: As used herein, the term "document" refers to an article comprising chemical information. The chemical information identifies, classifies, and/or describes (e.g., the structure of) one or more chemicals. In certain embodiments, a document is an article consisting entirely of one or more chemical structure representations. Document data corresponding to a document can be stored and/or indexed in a database such that a user may search for the document and/or for the contents of the document. A document may comprise additional elements such as text or images, for example, that provide additional chemical information.

Text data: As used herein, the term "text data" refers to data corresponding to text that does at least one of identify, classify, and describe a chemical and/or its structure. In some embodiments, a user inputs text data in a graphical user interface using a text field or text box. In certain embodiments, text data is stored as a string, wherein the string is a sequence of alphanumeric characters. Text data may be natural language words or phrases.

Associate, Associated with: As used herein, the terms "associate," and "associated with," as in a first data structure is associated with a second data structure, refer to a computer representation of an association between two data structures or data elements that is stored electronically (e.g., in computer memory). In some embodiments, a first data structure is stored on a first computer readable medium, a second data structure is stored on a second computer readable medium, and the association between the first data structure and second data structure is stored on the first computer readable medium. In some embodiments, a first data structure is stored on a first computer readable medium, a second data structure is stored on a second computer readable medium, and the association between the first data structure and second data structure is stored on the second computer readable medium.

String tag: As used herein, the term "string tag" refers to data comprising a string of alphanumeric characters used in identifying, classifying, and/or describing a chemical structure. In certain embodiments, the string of alphanumeric characters is a natural language sequence of alphanumeric characters.

Graphical Control Element: As used herein, the term "graphical control element" refers to an element of a graphical user interface element that may be used to provide user and/or individual input. A graphical control element may be a textbox, dropdown list, radio button, data field, checkbox, button (e.g., selectable icon), list box, or slider.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Systems and methods described herein relate to indexing and searching of sets of documents comprising chemical information using efficient methods. Document data corresponding to the sets of documents comprise chemical structure data that correspond to chemical structures referred to in the documents. Chemical structure data is used to generate string tags (e.g., words or phrases) that are associated with the chemical structure data and/or the document data. String tags are used to identify, classify, or describe the corresponding chemical structures and/or their representations in the documents. The use of string tags facilitates searching of both chemical structure information and text in a document by fast text-based search methods. The use of string tags in indexing a document also allows chemical structure representations in that document to be searched using text-based methods.

A user query comprising chemical structure data and text data, wherein the query is augmented to comprise one or more string tags based on the chemical structure data, allows a user's chemical structure representation input and text input to be searched simultaneously. Simultaneous searching can narrow the set of possibly relevant documents quickly. Simultaneous searching of chemical structures and descriptive text in a document efficiently provides a user with relevant search results faster than sequential searching of chemical structures and descriptive text (in either order).

In certain embodiments, the documents to be indexed and searched are stored as a database. A database of document data may be stored and indexed on a non-transitory computer readable medium for use in searching. The database may be locally accessible to a user from a computing device. For example, the user may use a database stored on a desktop computer, laptop computer, mobile device, tablet, or similar. The database may also be stored on a separate storage medium such as a compact disk, hard disk, or flash memory. In certain embodiments, the database is stored on a server or similar computing device accessible over a network (e.g., as a cloud computing service). A database may be stored remotely due to its large size or for consideration to scalability, for example. In certain embodiments, document data are stored in an indexing engine. In certain embodiments, document data is stored in a fault tolerant store. In certain embodiments, indexing data for indexed document data is stored and searched in a database with the document data being stored in one or more separate locations. In certain embodiments, a database is queried using a web-based interface.

Documents are indexed in a format such that they can be fully searched with text-based searching methods. Document data corresponding to the documents to be indexed may be loaded (e.g., uploaded) to a service such as ChemSearch. FIG. 1 shows an exemplary hierarchy of data structures that correspond to a document. Document data 100 comprise chemical structure data 110, text data 130, and metadata 140. Chemical structure data 110 corresponds to chemical structure information, such as a chemical structure representation. Chemical structure data may be stored in any number of standard formats (e.g., a simplified molecular input line entry specification (SMILES) or SMILES arbitrary target specification (SMARTS) based string or as formatted binary data). Chemical structure data 110 comprises bit-screening data 150 and connection data 160. Bit-screening data 150 correspond to one or more constituent elements of a chemical structure. Connection data 160 correspond to one or more connections (e.g., interactions, bonds) between a plurality of the one or more constituent elements. In certain embodiments, chemical structure data (e.g., bit-screening data and connection data) are stored as strings or converted to strings such that all document data used for searching is searchable with a text search engine.

Text data 130 corresponds to descriptive information about the chemical and/or its structure. For example, text data may describe properties of a chemical (e.g., its structure) and/or it may describe processes, reactions, or formulations/mixtures involving the chemical. In certain embodiments, document data may include metadata that can be used to identify the document and its contents. For example, a document's metadata may include a unique ID and bucket ID. The metadata may be persisted to allow the document to be referenced in a database.

Document data 100 has been augmented during indexing to comprise string tags 120 (as depicted by the dashed line connecting the two in FIG. 1). String tags are a sequence of characters that provide an alphanumeric text-based string for identifying, classifying, and/or describing chemical structures corresponding to chemical structure data in document data. In certain embodiments, string tags are generated using bit-screening data by performing an atom-by-atom or similar structure-based search on the bit-screening data therein to identify constituent elements corresponding to the bit-screening data and populating the string tags with strings in a predefined list or array that identify, classify, and/or describe the constituent elements. In certain embodiments, string tags are populated using an array that comprises the strings and corresponding reference bit screening data that is compared to the bit screening data in document data. The predefined list may be manually created by storing strings for common constituent elements in chemical structures and associations to reference bit-screening data that correspond to those common constituent elements. Thus, the reference bit-screening data associated with the pre-defined strings can be matched, using the structure-based search, to bit-screening data in document data in order to generate string tags that are populated with appropriate descriptive strings from the pre-defined list for constituent elements corresponding to the bit-screening data in the document data. String tags may also be generated using appropriate ad hoc structure-based methods that populate the string tags with appropriate descriptive strings. String tags may be associated with chemical structure data or directly with directly with the document data that comprises the chemical structure data. Referring again to FIG. 1, string tags 120 are associated with document data 100, but not directly associated with chemical structure data 110.

In certain embodiments, string tags are natural language words or phrases that a user may use to describe the associated chemical structure or substructure. For example, chemical structure data corresponding to pyridine (e.g., corresponding to a structural representation of pyridine or embedded chemical structure data corresponding to pyridine) could be associated with string tag "aromatic." Other examples of string tags that may be associated with chemical structure data are common names for constituent elements (e.g., functional groups or heteroatoms) present in the corresponding chemical structure. For example, acetone could be associated with string tag "ketone" or chloroform could be associated with string tag "chlorine" and/or "contains chlorine."

Figure 2:
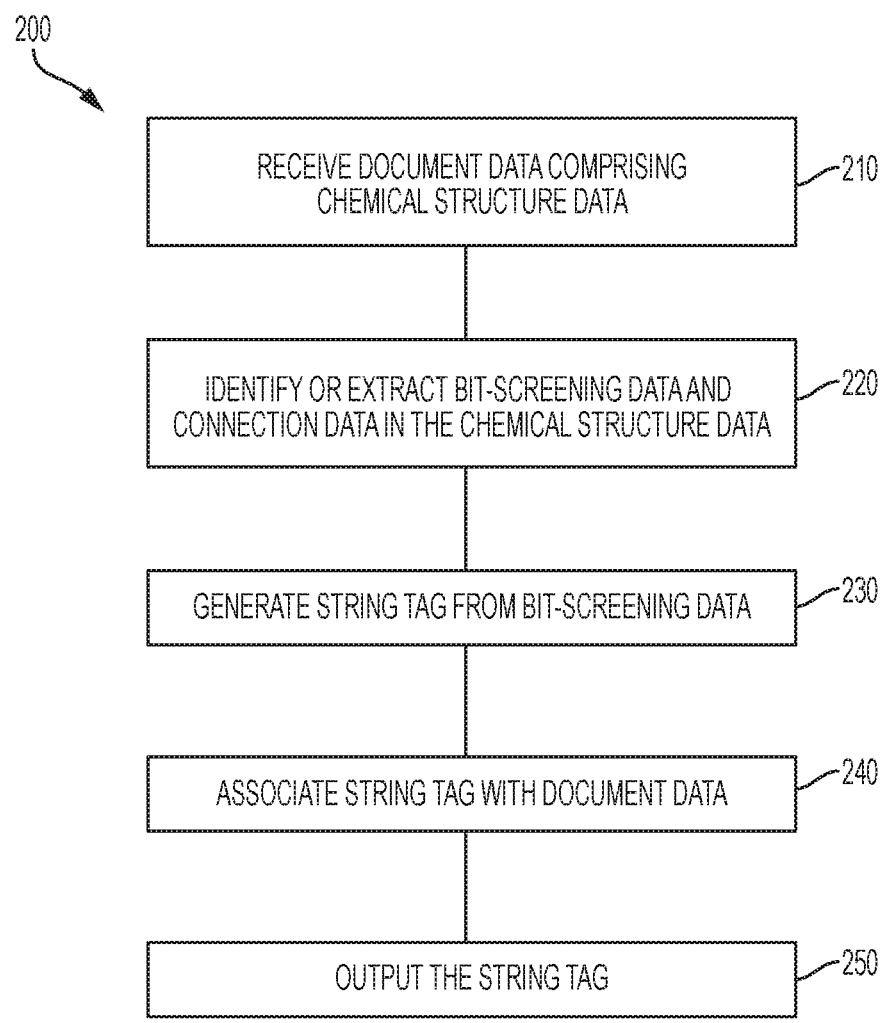
FIG. 2 is a block diagram of a method for indexing documents comprising chemical structure data, according to an illustrative embodiment of the present invention.

FIG. 2 is a block diagram of an exemplary method for indexing documents comprising chemical structure information. Indexing method 200 is used to augment document data by generating one or more string tags from chemical structure data in the document data. In step 210, document data comprising chemical structure data is received by a processor of a computing device. In step 220, bit-screening data and connection data in the chemical structure data is identified or extracted. In step 230, the bit-screening data identified or extracted in step 220 is used to generate a string tag. In step 240, the string tag generated in step 230 is associated with the document data directly. In step 250, the string tag is outputted. The string tag outputted in step 250 is stored with the document data for later searching. In some embodiments, document data is augmented to comprise a string tag. In some embodiments, a string tag is stored separate from document data. When a string tag is stored separate from document data, the document data may be augmented to comprise the association of the string tag to the document data such that the string tag is searchable when the document data is being searched.

Document data may be received by uploading it to an internal configured search provider service. A search provider is an abstraction layer that is configured to one or more specific search engines. A configured search provider may be modified to work with a different specific search engine without interfering with other aspects of the search process. In certain embodiments, there is only one configured search provider in the search provider service. In certain embodiments, the internal configured search provider service persists metadata in the document data throughout the indexing process.

To identify or extract bit-screening data and connection data, the configured search provider can call a chemical search core engine to identify or extract chemical structure data. The chemical search core engine can identify or extract data within the document data that corresponds to chemical structures if the data are stored in a standard format recognized by the engine. The chemical search core engine extracts both bit-screening and connection data. Bit-screening data correspond to the constituent elements of the chemical structure and can be used to search for those constituent elements of the corresponding chemical structure identified in the chemical structure data. Connection data is stored for use in any supplementary structure-based searching that may follow a text-based search. The bit-screening data are used to generate string tags to allow chemical structure data of interest to a user to be identified using text-based search methods by correlating string tags corresponding to chemical structure data with a user query. Connection data may be stored as an encoded string. In certain embodiments, connection data and bit-screening data in document data are converted to strings during indexing in order to allow all searching (e.g., text searching and structure searching) to be performed using a text search engine.

Once a chemical search core engine has extracted or identified chemical structure data and augmented the chemical structure data (i.e., connection data and bit-screening data) to appropriate strings (i.e., encoded strings and string tags, respectively), the string tag is outputted. The document data may be augmented with the outputted string tag. The document data may initially be augmented with the encoded strings converted from the connection data. The augmented data is sent to the underlying indexing engine. The outputted string tags are indexed just like other text data such that text data input by a user could be correlated with a string tag to identify a search result when searching. Connection data are not indexed, but are stored with the document for retrieval during a search workflow. In certain embodiments, connection data or converted connection data are used in structure-based searches run subsequent to an initial text-based search. After indexing a document in a database, the document data are available to be searched by a user.

Figure 7:
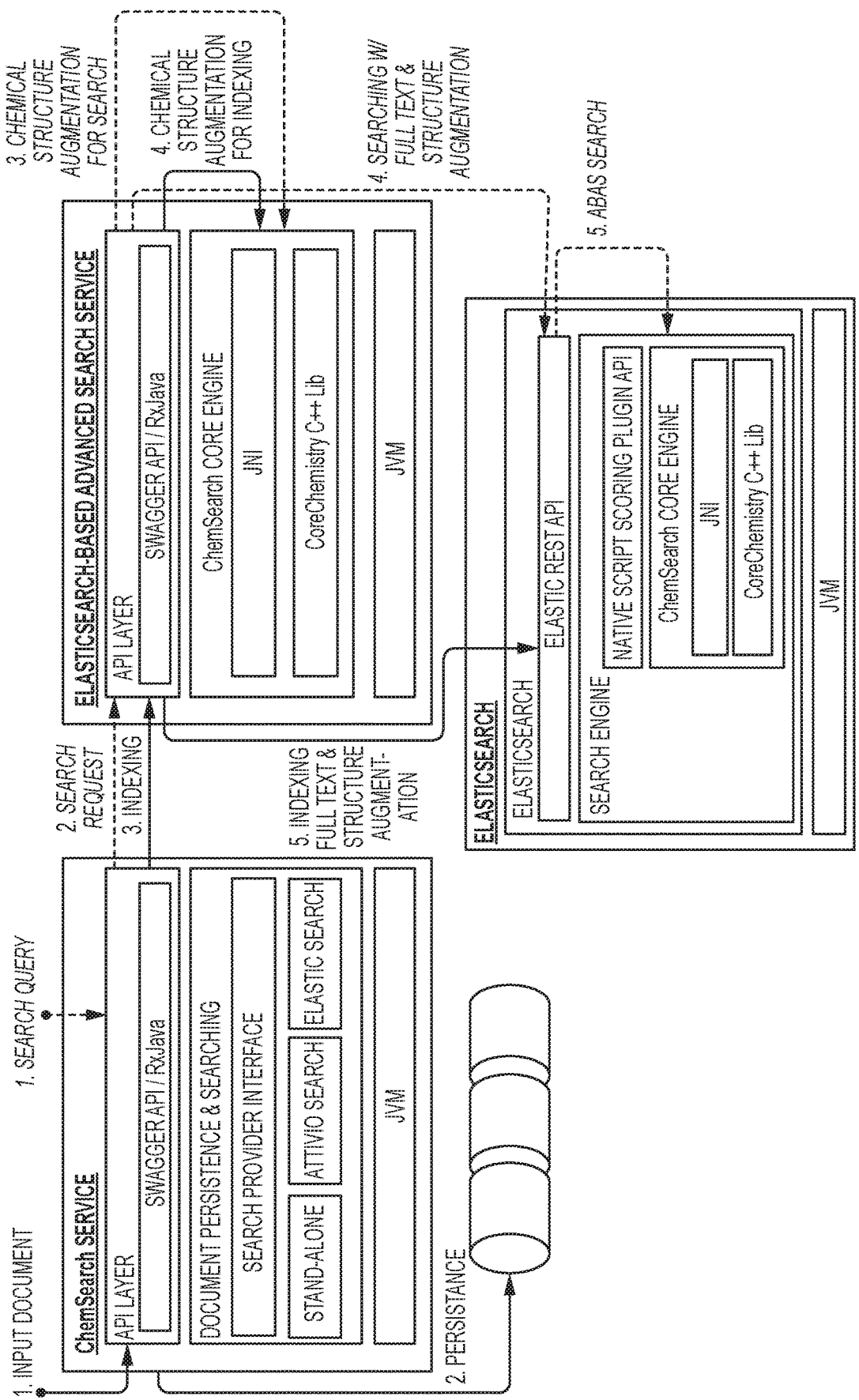
FIG. 7 is an exemplary system of software modules that can be used for indexing and searching documents comprising chemical information, according to an illustrative embodiment of the present invention.

An embodiment of an integrated internally configured chemical search provider service module (e.g., ChemSearch Service) with an Elasticsearch-based advanced search service module (comprising a chemical search core engine) and search engine module in indexing documents is depicted in FIG. 7. The document data is input into the ChemSearch service for processing. Processing comprises persisting the metadata in the document data. The document data is indexed and sent to the Elasticsearch-based advanced search service. The ChemSearch core engine in the Elasticsearch-based advanced search service is used to generate string tags for the chemical structure data in the document data being indexed and augments the document data to comprise the string tags. The indexed and augmented document data is then sent to the Elasticsearch module.

In certain embodiments, a ChemSearch service is integrated into the searching workflow. In certain embodiments, a ChemSearch service is tightly integrated. A tightly integrated search integration means that all searches (i.e., any text and structure searches) can be handled by one search module (e.g., a ChemSearch service). In certain embodiments, a ChemSearch service is supplementary. In a supplementary integration, a main search engine performs most searching, while an auxiliary search engine performs chemical data searches. The auxiliary search engine is invoked only when a structure-based search is requested. In certain embodiments, an auxiliary search engine is built by indexing only a subset of document data (e.g., metadata).

A user searching for documents of interest provides input into a search interface. Search input may be provided using an interface locally run on a computing device or may be accessed using a web-based interface. The user may be searching for some or all documents in a database that comprise information about a particular chemical structure. In general, a user is searching for documents that comprise information about a genus of chemical structures identified by a set of constituent elements and/or a list of properties of the structure (e.g., related to its functionality, reactivity, or production). The genus of interest may be specific, including few members constrained by the presence of a plurality of constituent elements, or it may be broad, including many members with only one or a few common constituent elements. For example, a user may be interested in a genus of complex chemical structures where only a terminal group of the structure differs between members of the genus or the user may be interested in all chemical structures that are aromatic.

In certain embodiments, the search interface provided to the user comprises one or more text fields for inputting text data and a subinterface for inputting chemical structure data. The user can input any descriptive text into the one or more text fields. Descriptive text provided by the user may refer to the properties of chemical structures of interest or the structure of the chemical structure itself. For example, the user may input "yield of more than 90%" or "contains three carbonyl groups" as descriptive text. When the user is interested in complex chemical structures, it is impractical for the user to describe a chemical structure sufficiently using natural language to produce relevant results. A subinterface for entering chemical structures may be used by the user to draw or similarly input a chemical structure or partial chemical structure to be used in searching a database. In some embodiments, the subinterface for drawing chemical structures is a ChemDraw® (by PerkinElmer Informatics, Inc. of Cambridge, Mass.) interface. Chemical structure data may be input as a chemical structure representation, into a text field using a line notation string (e.g., a simplified molecular input line entry specification (SMILES) or SMILES arbitrary target specification (SMARTS) based string). In this way, whether a user provides chemical structure input or descriptive text input to identify chemical structures of interest in a search, the chemical structure can be searched for using a text-based method.

Figure 8:
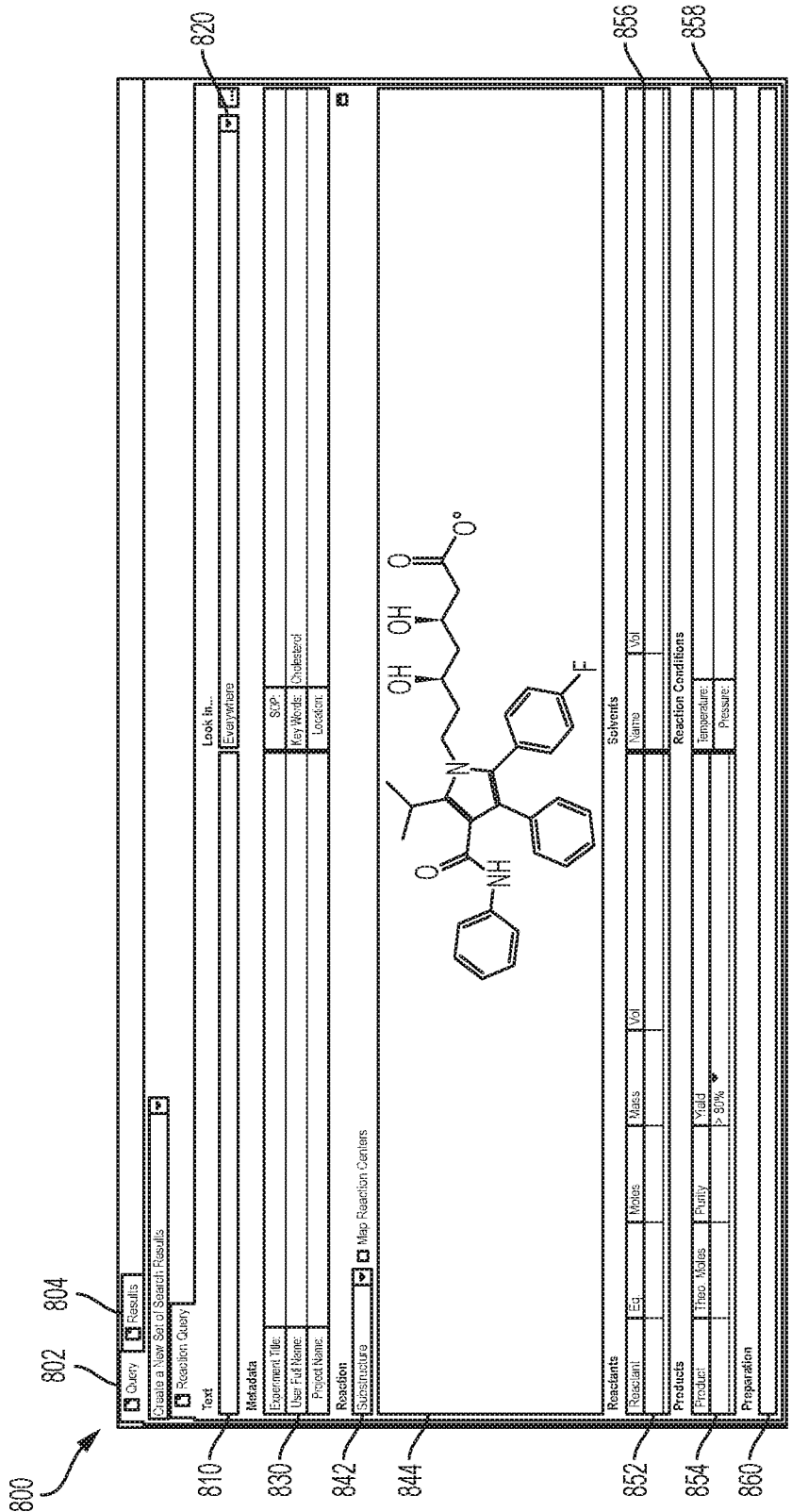
FIG. 8 is a screenshot of an interface used to input user queries and view search results, according to an illustrative embodiment of the present invention.

FIG. 8 shows a screenshot of an exemplary search interface by which a user inputs a query and views search results in some embodiments. Search interface 800 has two tabs: query tab 802 for use in entering queries and results tab 804 for viewing results of a search. Query tab 802 comprises a plurality of graphical control elements for entering terms to be used in a search. Text field 810 provides a graphical control element for the user to input alphanumeric text to be used in searching. Dropdown list 820 is a graphical control element that allows a user to select a database, set of databases, or subset(s) of one or more databases to search over. Text fields 830 are a plurality of graphical control elements for inputting various metadata terms to be included in a user query. In certain embodiments, a search is performed over only a subset of documents that comprise metadata that matches, or corresponds within some threshold, to the user input metadata values. For example, a user may input a particular project name such that the user query is only searched for in documents associated with metadata of that project name.

Graphical control elements 842 and 844 are used to input chemical structure data by drawing one or more chemical structures. Clicking on graphical control element 844 provides to the user a separate interface that allows chemical structures to be drawn (e.g., having tools that draw bonds and chemical constituents). For example, clicking graphical control element 844 may open a ChemDraw® (by PerkinElmer Informatics, Inc. of Cambridge, Mass.) interface. Dropdown list 842 is used to select the type of structure being drawn. For example, dropdown list 842 allows a user to select from "substructure," "complete structure," and "multiple structures." The selection from this list is used to properly generate string tags and run search algorithms. Dropdown list 842 shows "substructure" is selected. Graphical control element 844 shows a substructure drawn by a user as part of a user query.

Graphical control elements 852, 854, 856, 858, and 860 allow a user to input additional text data for specific characteristics of interest related to the chemical(s) being searched for. For example, a user may use text fields 852 to provide text data for reactants in a reaction related to the chemical(s) of interest. The user may input text data for reaction products in graphical control elements 854. For example, the user has selected a yield of more than eighty percent with graphical control elements 854. The user may input text data for solvents used in a reaction with text fields 856. The user may input text data for reaction conditions (e.g., temperature and pressure or ranges thereof) with text fields 858. The user may input text data for preparation criteria in text fields 860.

Graphical control elements 852, 854, 856, 858, and 860 are included in search interface 800 in addition to text field 810 to allow a user to input text data corresponding to particular characteristics of interest separately from general text data input into text field 810. For example, text based searching of string "yield >80%" (e.g., entered into text field 810) may produce results for all documents that mention yields over 80%, whereas selection of ">80%" in graphical control elements 854 will produce results only for documents in which the drawn chemical structure and/or input product is yielded at >80% yield in a reaction. Furthermore, in certain embodiments, search algorithms comprise multiple steps, wherein inputs into each of graphical control elements 810, 852, 854, 856, 858, and 860 are searched in separate steps. In certain embodiments, such segmented search algorithms accelerate search times and/or produce results of enhanced relevance to the user. Thus, in search interface 800, text field 810 allows a user to input general text data, while graphical control elements 852, 854, 856, 858, and 860 allow the user to input text data corresponding to specific characteristics related to the chemical(s) of interest to the user (e.g., corresponding to characteristics and/or conditions of a reaction). The text data of a user query, as used in searching as described herein, may include data input into any one or more of these graphical control elements. In some embodiments, all text data of a user query is input in a singular text field provided to a user in an interface.

Figure 3:
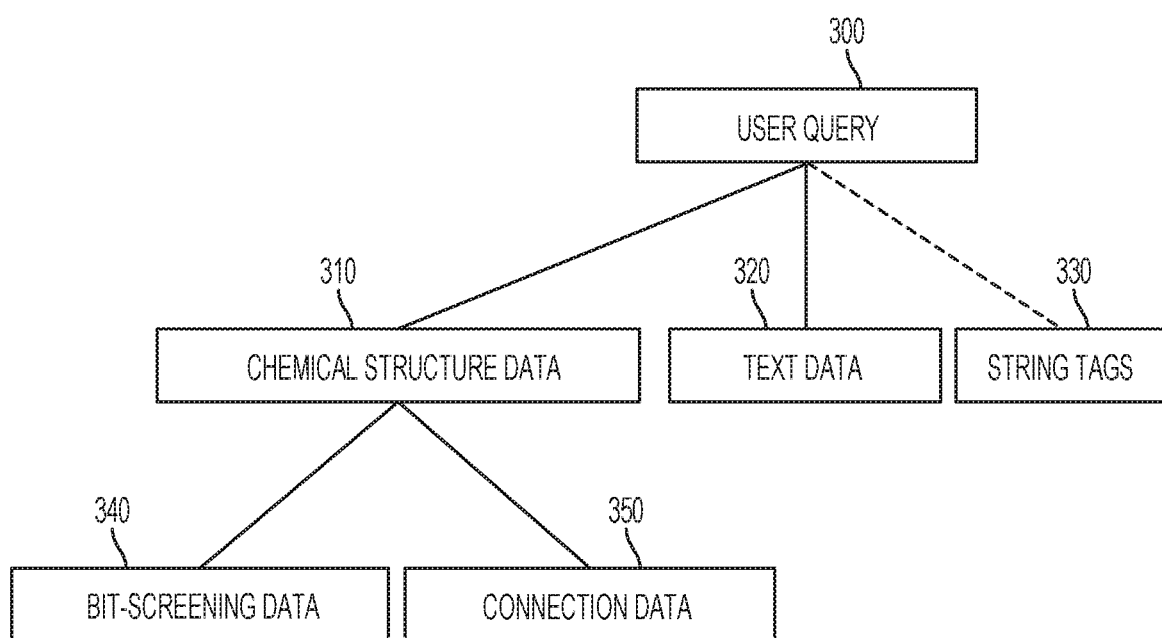
FIG. 3 shows a hierarchy of data structures corresponding to a user query, according to an illustrative embodiment of the present invention.

FIG. 3 shows a hierarchy of data structures associated with a user query. User query 300 comprises chemical structure data 310 and text data 320. Chemical structure data 310 comprises bit-screening data 340 and connection data 350. Bit-screening data 340 may be used to identify one or more constituent elements of the chemical structure corresponding to the associated chemical structure data in order to generate string tags 330. Once string tags 330 are generated, user query 300 is augmented to be associated with string tags 330. String tags 330 can be generated using a pre-defined list of strings as described herein above. User query 300 can be received by a processor of a computing device in order to query a database of document data using a text-based search method. In certain embodiments, a user query comprises both text data and chemical structure data. In certain embodiments, a user query comprises text data and not chemical structure data. In certain embodiments, a user query comprises chemical structure data and not text data.

Figure 4:
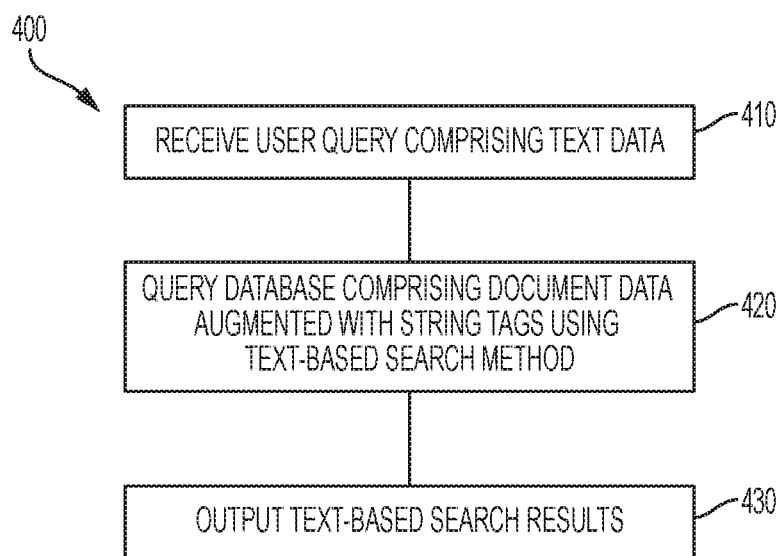
FIG. 4 is a block diagram of a method for searching documents augmented with string tags, according to an illustrative embodiment of the present invention.

FIG. 4 is a block diagram for a method of searching a database of augmented document data (i.e., the document data comprises string tags) using a user query comprising text data. Searching method 400 is used to perform a text-based search of a database of document data augmented with string tags using a user query comprising text data. In step 410, a processor of a computing device receives a user query comprises text data. In step 420, a database of document data augmented with string tags is queried using a text-based search method with the user query received in step 410 to generate text-based search results. The querying step includes correlating text data received as part of the user query in step 410 with string tags in the augmented document data using the text-based search method. In this way, documents that have chemical structure representations, but do not contain text explicitly identifying the chemical by a common name can be identified as a result in the querying step. For example, a representation of benzene may be present in a document, but the text of the document may only include the phrase "aromatic ring." Because the corresponding document data was augmented to comprise a string tag comprising the string "benzene" as a result of indexing (e.g., according to the method of FIG. 2), searching method 400 would identify the document as a result for a user query comprising the text data "benzene." In step 430, the text-based search results generated in step 420 are output, for example, for displaying to a user or for further processing.

Figure 5:
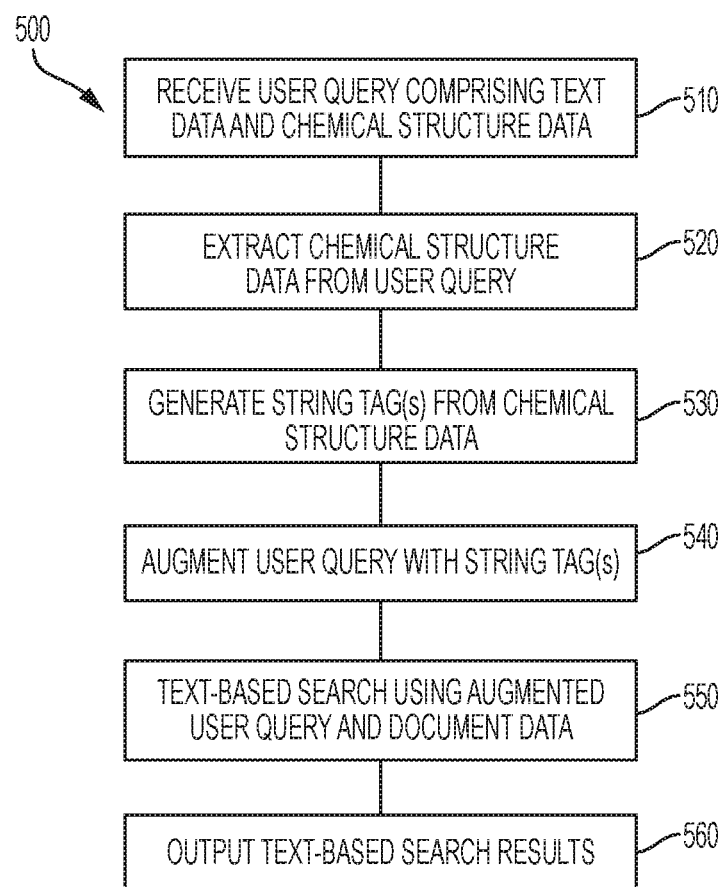
FIG. 5 is a block diagram of a method for augmenting a user query comprising chemical structure data to search a set of documents using a text-based search, according to an illustrative embodiment of the present invention.

FIG. 5 is a block diagram for a method of searching a database of document data using a user query comprising text data and chemical structure data. Searching method 500 is used to perform a text-based search of a database of document data augmented with string tags using a user query comprising text data. Text-based search results may be output for displaying to a user or for further processing. Text-based search results may be stored for later reference. In step 510, a processor of a computing device receives a user query comprising text data and chemical structure data. The user query may be sent to the processor from another computing device used by a user to input the text data and chemical structure data using an interface as described herein above. In step 520, chemical structure data is extracted from the user query received in step 510. In step 530, the extracted chemical structure data is used to generate the string tag(s). String tags generated from chemical structure data in a user query can be generated using the same methods for generating string tags during document indexing, as described herein above. In certain embodiments, chemical structure data is extracted from the user query to generate the string tag(s). In some embodiments, chemical structure data in the user query is identified to generate the one or more string tag(s). In step 540, the user query is augmented with the string tag(s) generated in step 530. In step 550, a text-based search is performed using the augmented user query and the document data corresponding to the documents being searched. Any text-based search method that allows any two strings (i.e., any string of the user query and any string in the document data) to be correlated with each other may be used in step 550. For example, the text-based search method could generate results using a relevance search or hit ranking search algorithm. In step 560, the text-based search results generated in step 550 are output, for example, for displaying to a user or for further processing.

The text-based search method used in step 550 can correlate any string of the user query with any string of the document data in order to generate a search results. By augmenting the user query with string tag(s) in step 540, chemical structure data input by a user that may not be input in a string-based format can be used to perform the text-based search. That is, a string tag in the augmented user query can be correlated with a string (e.g., text data) in document data to generate a result. Thus, search results that may not have been generated without the query augmentation can be provided to the user. The string in the document data user to generate the text-based search result may be in a string tag in the document data generated during indexing. In this way, chemical structure data in document data that is stored in one format can be searched against chemical structure data input in the user query in another format. Likewise, document data that has been augmented to comprise one or more string tags during indexing can be identified as a result for a user query by correlating either a portion of the text data in the user query or a portion of the string tag(s) generated from the chemical structure data in the user query.

A user query comprising chemical structure data but not text data can be augmented and used for searching according to method 500. When a user query comprises chemical structure data, but not text data, text-based search results are generated by correlating at least a portion of the string tag(s) in the augmented user query with document data. In some embodiments, a user query comprising chemical structure data, but not text data is augmented to comprise string tag(s) and at least a portion of the string tag(s) are correlated with at least a portion of index string tags in augmented document data (e.g., where the index string tags were added to the document data during indexing). Thus, fast text-based searches can be performed on user queries consisting entirely of chemical structure data to return results that describe chemicals using only text or only chemical structure representations. This is in contrast to current methods that require slower structure-based methods to be used for user queries consisting entirely of chemical structure data.

For user queries comprising text data and chemical structure data, text-based search methods can search a database to produce results by searching for relevant documents simultaneously using the text data of the user query and string tags generated from the chemical structure data of the user query. This eliminates the sequential text-based then structure-based searching (or visa-versa) required by a traditional (i.e., unaugmented) user query. Without wishing to be bound by any theory, such sequential searching is rate limited by the speed of the structure-based searching step. The text-based search results of method 500 or similar are influenced by all the information provided in the user query such that the text-based search results more accurately relate to information sought by the user.

Figure 6:
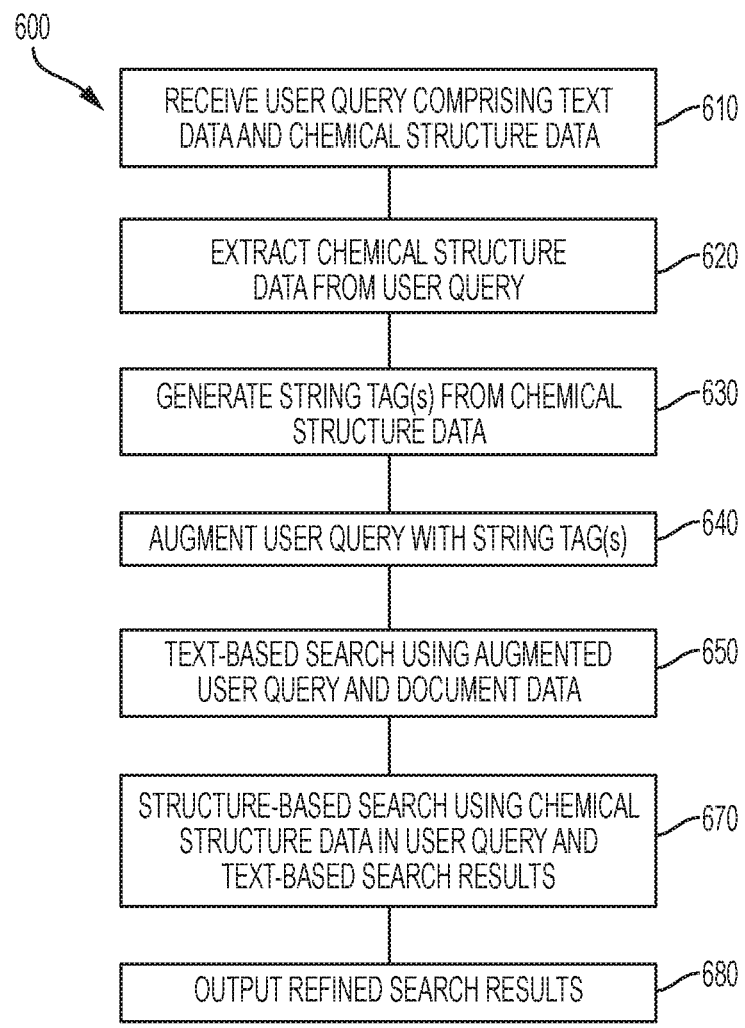
FIG. 6 is a block diagram of a method for augmenting a user query comprising chemical structure data to efficiently search a set of documents using a text-based search then a structure-based search, according to an illustrative embodiment of the present invention.

For some searches, even the text-based search results produced by a text-based search method that simultaneously searches text data and chemical structure data in a user query are too broad or inconclusive for a user. FIG. 6 shows a method for searching, using a structure-based search method, the results of a text-based search based on a user query comprising text data and chemical structure data (e.g., according to method 500). Steps 610-650 of method 600 are the same as steps 510-550 of method 500. In step 670, the text-based search results generated in steps 610-650 are used to perform a structure-based search of the text-based search results based on the chemical structure data of the user query. In certain embodiments, a structure-based search is performed in a text search engine such that all searching can be performed using a single search engine. In order for a single text search engine to be used for structure-based searches and text-based searches, connection data and bit-screening data in document data are converted to strings during indexing. The refined search results are output in step 680, for example, for displaying to a user or for further processing.

The structure-based search may be an atom-by-atom search or any other structure-based search known in the art that produces results related to chemical structures that exactly or near exactly match the chemical structure of interest to the user (i.e., that correspond to the chemical structure data supplied by the user). In some embodiments, the chemical structure data in the document data of the text-based search results are combined into an in-memory minimum spanning tree such that the structure-based search consists of searching the in-memory minimum spanning tree using the chemical structure data of the query. The use of minimum spanning trees can reduce the expense (e.g., time, processing capacity) of subsequent structure-based searches. The structure-based search correlates the user-input chemical structure data of the user query with the relevant chemical structure data of the text-based search results.

Filtering the document data to be searched over with a structure-based method by firstly text-based searching the document data simultaneously using an augmented user query comprising text data and string tags can increase the speed of the structure-based search method in proportion to the smallness of the set of filtered document data. For searches where the use of string tags greatly reduces the amount of document data resulting from the text-based search (compared to what is achievable with text data alone), the structure-based search is quite fast. The speed of such a subsequent structure-based search is quite fast because the amount document data being searched over in the structure-based search is greatly reduced from the initial amount of document data (i.e., prior to the text-based search). The chemical structure data of the user query can quickly be correlated with the relevant chemical structure in the filtered document data (i.e., the data of the text-based search results).

The use of a text-based search method prior to a subsequent structure-based search without the use of string tags will often not significantly limit the amount of document data the structure-based search is searched over. For example, if a user wants to find documents that relate to methods to produce a genus of chemicals with reaction yields over 90%, the user may supply a partial or complete representation of the genus and the text "yield over 90%." If the text data is used in a first text-based search method without string tags (as in an augmented user query), the document data of the text-based search results includes a large amount of data for documents that relate to processes with yields over 90% involving chemical structures that aren't of interest to the user. Any subsequent structure-based search will be performed on the irrelevant data in addition to any relevant data returned by the text-based search, thus slowing down the overall searching method.

If string tags generated based on the chemical structure data of the user query are used in the text-based search (e.g., using method 600), a significant portion (and up to all) of the irrelevant document data is be excluded from searching in the subsequent structure-based search. The subsequent structure-based search can refine the text-based search results to include only those comprising chemical structure representations of at least a certain degree of similarity to the input chemical structure representation. The use of a subsequent structure-based search to refine search results is especially useful for searches where the user inputs complex chemical structure representations. Performing a structure-based search based on an augmented user query comprising chemical structure data corresponding to a complex chemical structure refines the search results to exclude those text-based search results that only have lesser similarity with the complex chemical structure (e.g., enough to produce a correlation with a string tag in the augmented user query).

A user query may be received by API call to an internal configured search provider service. To identify or extract bit-screening data and connection data, the configured search provider can call a chemical search core engine to identify or extract chemical structure data. The chemical search core engine can identify or extract data within the document data that corresponds to chemical structures if the data are stored in a standard format recognized by the engine. The chemical search core engine extracts both bit-screening and connection data. Bit-screening data correspond to the constituent elements of the chemical structure and can be used to search for those constituent elements of the chemical structure corresponding to the chemical structure data. Connection data is stored for use in any supplementary structure-based searching that may follow a text-based search. The bit-screening data are used to generate string tags to allow chemical structure data of interest to a user to be identified using text-based search methods by correlating string tags corresponding to chemical structure data with a user query. Connection data may be stored as an encoded string.

Once a chemical search core engine has extracted or identified chemical structure data and converted the chemical structure data (i.e., connection data and bit-screening data) to appropriate strings (i.e., encoded strings and string tags, respectively), the string tag is outputted. The user query is augmented with the outputted string tag. The augmented user query is sent to the underlying searching engine. The string tags can be treated as user-input text data during searching. After a chemical search core engine has been used to augment the user query, the augmented user query can be sent to a search engine for searching. A search engine performs a text-based search and, optionally, a structure-based search using an atom-by-atom based search method to provide search results to a user.

The use of an integrated internal configured search provider service (e.g., ChemSearch Service) module with an Elasticsearch-based advanced search service module (comprising a chemical search core engine) and search engine module in searching documents is depicted in FIG. 7. The user query is input into the ChemSearch service for processing. The search request is sent to the Elasticsearch-based advanced search service. The ChemSearch core engine in the Elasticsearch-based advanced search service is used to generate string tags for the chemical structure data in the user query being searched and augment the query to comprise the string tags. The augmented user query is then sent to the Elasticsearch module for searching using text-based searching and atom-by-atom searching to produce search results to the user.

Figure 9:
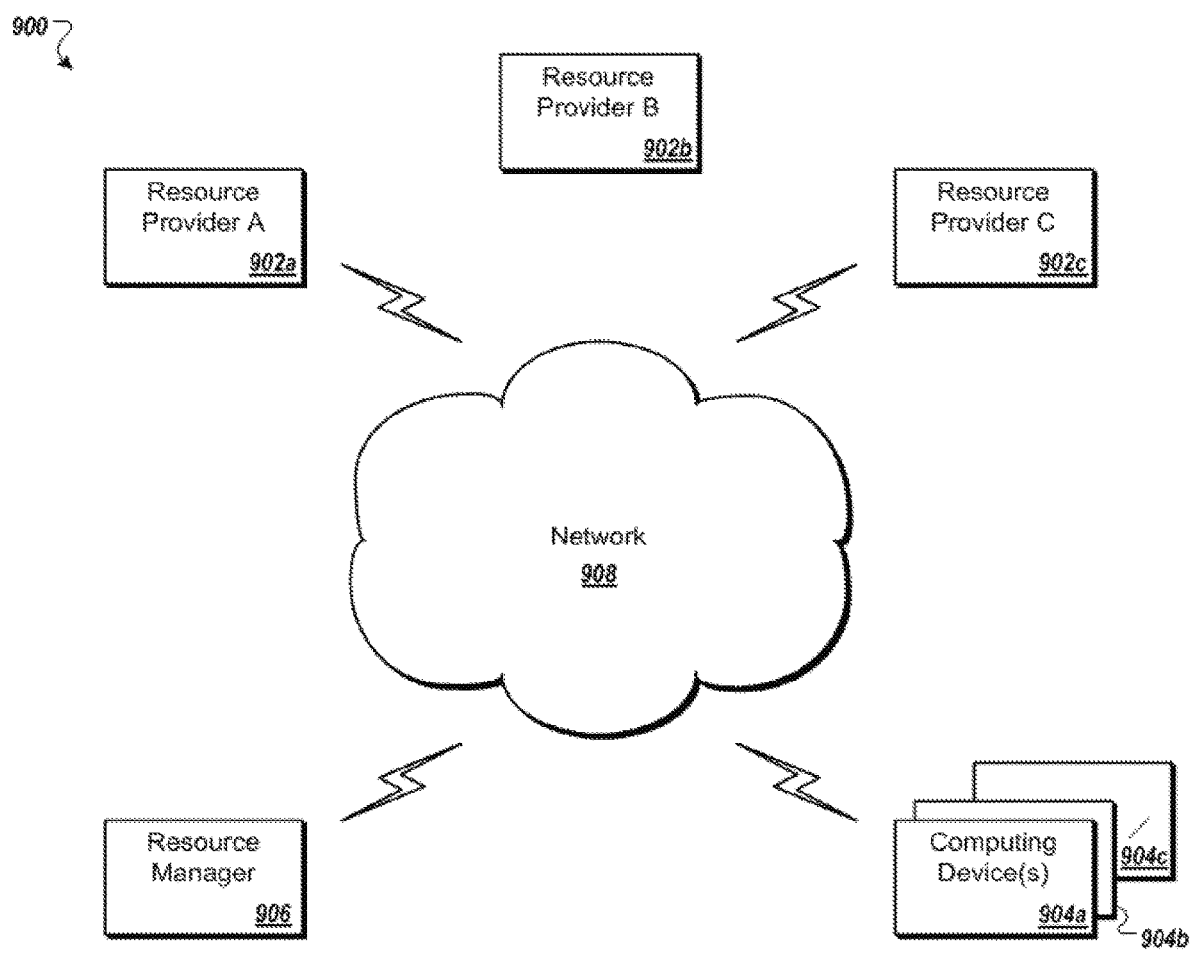
FIG. 9 is a block diagram of an example network environment for use in the methods and systems described herein, according to an illustrative embodiment.

FIG. 9 shows an illustrative network environment 900 for use in the methods and systems described herein. In brief overview, referring now to FIG. 9, a block diagram of an exemplary cloud computing environment 900 is shown and described. The cloud computing environment 900 may include one or more resource providers 902a, 902b, 902c (collectively, 902). Each resource provider 902 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 902 may be connected to any other resource provider 902 in the cloud computing environment 900. In some implementations, the resource providers 902 may be connected over a computer network 908. Each resource provider 902 may be connected to one or more computing device 904a, 904b, 904c (collectively, 904), over the computer network 908.

The cloud computing environment 900 may include a resource manager 906. The resource manager 906 may be connected to the resource providers 902 and the computing devices 904 over the computer network 908. In some implementations, the resource manager 906 may facilitate the provision of computing resources by one or more resource providers 902 to one or more computing devices 904. The resource manager 906 may receive a request for a computing resource from a particular computing device 904. The resource manager 906 may identify one or more resource providers 902 capable of providing the computing resource requested by the computing device 904. The resource manager 906 may select a resource provider 902 to provide the computing resource. The resource manager 906 may facilitate a connection between the resource provider 902 and a particular computing device 904. In some implementations, the resource manager 906 may establish a connection between a particular resource provider 902 and a particular computing device 904. In some implementations, the resource manager 906 may redirect a particular computing device 904 to a particular resource provider 902 with the requested computing resource.

Figure 10:
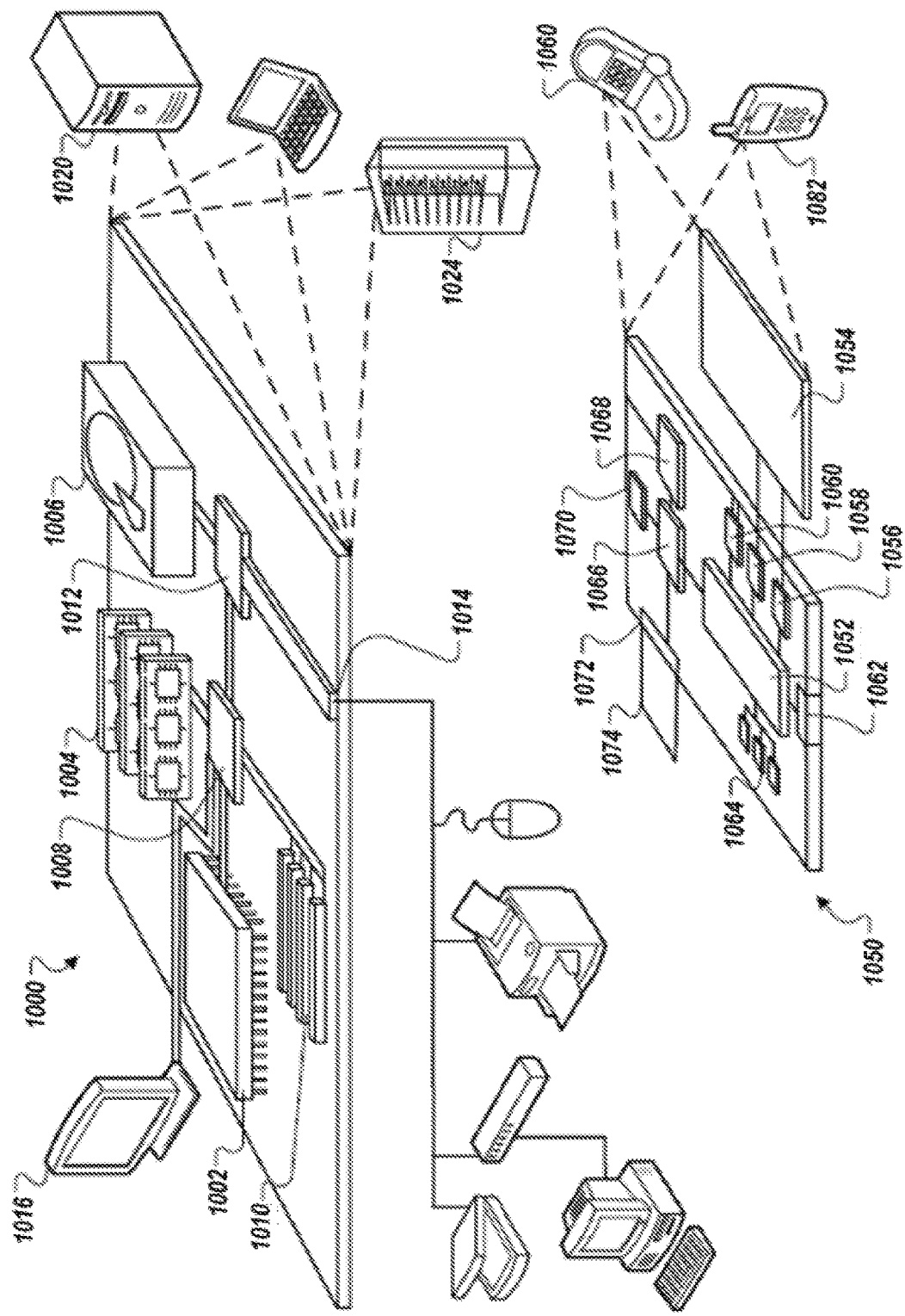
FIG. 10 is a block diagram of an example computing device and an example mobile computing device, for use in illustrative embodiments of the invention.

FIG. 10 shows an example of a computing device 1000 and a mobile computing device 1050 that can be used in the methods and systems described in this disclosure. The computing device 1000 is intended to represent various forms of digital computers, such as laptops, desktops, workstations, personal digital assistants, servers, blade servers, mainframes, and other appropriate computers. The mobile computing device 1050 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1000 includes a processor 1002, a memory 1004, a storage device 1006, a high-speed interface 1008 connecting to the memory 1004 and multiple high-speed expansion ports 1010, and a low-speed interface 1012 connecting to a low-speed expansion port 1014 and the storage device 1006. Each of the processor 1002, the memory 1004, the storage device 1006, the high-speed interface 1008, the high-speed expansion ports 1010, and the low-speed interface 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as a display 1016 coupled to the high-speed interface 1008. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1004 stores information within the computing device 1000. In some implementations, the memory 1004 is a volatile memory unit or units. In some implementations, the memory 1004 is a non-volatile memory unit or units. The memory 1004 may also be another form of computer-readable medium, such as a magnetic or optical disk.

The storage device 1006 is capable of providing mass storage for the computing device 1000. In some implementations, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1002), perform one or more methods, such as those described above. The instructions can also be stored by one or more storage devices such as computer- or machine-readable mediums (for example, the memory 1004, the storage device 1006, or memory on the processor 1002).

The high-speed interface 1008 manages bandwidth-intensive operations for the computing device 1000, while the low-speed interface 1012 manages lower bandwidth-intensive operations. Such allocation of functions is an example only. In some implementations, the high-speed interface 1008 is coupled to the memory 1004, the display 1016 (e.g., through a graphics processor or accelerator), and to the high-speed expansion ports 1010, which may accept various expansion cards (not shown). In the implementation, the low-speed interface 1012 is coupled to the storage device 1006 and the low-speed expansion port 1014. The low-speed expansion port 1014, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. In addition, it may be implemented in a personal computer such as a laptop computer 1022. It may also be implemented as part of a rack server system 1024. Alternatively, components from the computing device 1000 may be combined with other components in a mobile device (not shown), such as a mobile computing device 1050. Each of such devices may contain one or more of the computing device 1000 and the mobile computing device 1050, and an entire system may be made up of multiple computing devices communicating with each other.

The mobile computing device 1050 includes a processor 1052, a memory 1064, an input/output device such as a display 1054, a communication interface 1066, and a transceiver 1068, among other components. The mobile computing device 1050 may also be provided with a storage device, such as a micro-drive or other device, to provide additional storage. Each of the processor 1052, the memory 1064, the display 1054, the communication interface 1066, and the transceiver 1068, are interconnected using various buses, and several of the components may be mounted on a common motherboard or in other manners as appropriate.

The processor 1052 can execute instructions within the mobile computing device 1050, including instructions stored in the memory 1064. The processor 1052 may be implemented as a chipset of chips that include separate and multiple analog and digital processors. The processor 1052 may provide, for example, for coordination of the other components of the mobile computing device 1050, such as control of user interfaces, applications run by the mobile computing device 1050, and wireless communication by the mobile computing device 1050.

The processor 1052 may communicate with a user through a control interface 1058 and a display interface 1056 coupled to the display 1054. The display 1054 may be, for example, a TFT (Thin-Film-Transistor Liquid Crystal Display) display or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may provide communication with the processor 1052, so as to enable near area communication of the mobile computing device 1050 with other devices. The external interface 1062 may provide, for example, for wired communication in some implementations, or for wireless communication in other implementations, and multiple interfaces may also be used.

The memory 1064 stores information within the mobile computing device 1050. The memory 1064 can be implemented as one or more of a computer-readable medium or media, a volatile memory unit or units, or a non-volatile memory unit or units. An expansion memory 1074 may also be provided and connected to the mobile computing device 1050 through an expansion interface 1072, which may include, for example, a SIMM (Single In Line Memory Module) card interface. The expansion memory 1074 may provide extra storage space for the mobile computing device 1050, or may also store applications or other information for the mobile computing device 1050. Specifically, the expansion memory 1074 may include instructions to carry out or supplement the processes described above, and may include secure information also. Thus, for example, the expansion memory 1074 may be provided as a security module for the mobile computing device 1050, and may be programmed with instructions that permit secure use of the mobile computing device 1050. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1052), perform one or more methods, such as those described above. The instructions can also be stored by one or more storage devices, such as one or more computer- or machine-readable mediums (for example, the memory 1064, the expansion memory 1074, or memory on the processor 1052). In some implementations, the instructions can be received in a propagated signal, for example, over the transceiver 1068 or the external interface 1062.

The mobile computing device 1050 may communicate wirelessly through the communication interface 1066, which may include digital signal processing circuitry where necessary. The communication interface 1066 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1068 using a radio-frequency. In addition, short-range communication may occur, such as using a Bluetooth®, Wi-Fi™, or other such transceiver (not shown). In addition, a GPS (Global Positioning System) receiver module 1070 may provide additional navigation- and location-related wireless data to the mobile computing device 1050, which may be used as appropriate by applications running on the mobile computing device 1050.

The mobile computing device 1050 may also communicate audibly using an audio codec 1060, which may receive spoken information from a user and convert it to usable digital information. The audio codec 1060 may likewise generate audible sound for a user, such as through a speaker, e.g., in a handset of the mobile computing device 1050. Such sound may include sound from voice telephone calls, may include recorded sound (e.g., voice messages, music files, etc.) and may also include sound generated by applications operating on the mobile computing device 1050.

The mobile computing device 1050 may be implemented in a number of different forms, as shown in the figure. For example, it may be implemented as a cellular telephone 1080. It may also be implemented as part of a smart-phone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Having described certain implementations of methods and systems for indexing and searching documents comprising chemical information it will now become apparent to one of skill in the art that other implementations incorporating the concepts of the disclosure may be used. Therefore, the disclosure should not be limited to certain implementations, but rather should be limited only by the spirit and scope of the following claims.

The invention claimed is:

1. A method comprising:
    receiving, by a computing device, document data corresponding to a document, wherein the document data comprises chemical structure data corresponding to a chemical structure, and the chemical structure data comprises a graphical representation of the chemical structure;
    determining, by the computing device, bit-screening data and connection data based on the chemical structure data, wherein:
        the bit-screening data corresponds to one or more constituent elements of the chemical structure, and
        the connection data corresponds to one or more connections between the one or more constituent elements of the chemical structure;
    determining, by the computing device, at least one string tag based on at least a portion of the bit-screening data, wherein the at least one string tag comprises an alphanumeric value for describing the chemical structure corresponding to the chemical structure data;
    determining, by the computing device, an association of the at least one string tag with the document data;
    outputting, by the computing device, the at least one string tag; and
    indexing, by the computing device, the document data based on the at least one outputted string tag, wherein the chemical structure data corresponding to a chemical structure in the document is searchable based on correlating at least a portion of text data of a query with the indexed document data.

2. The method of claim 1 further comprising:
    augmenting the document data to comprise the at least one outputted string tag.

3. The method of claim 1, wherein determining the at least one string tag comprises:
    performing an atom-by-atom search or a structure-based search on the bit-screening data to identify the one or more constituent elements corresponding to the bit-screening data; and
    populating the at least one string tag with one or more strings identifying, classifying, or describing the one or more constituent elements.

4. The method of claim 1, wherein determining the at least one string tag comprises:
    converting the bit-screening data into one or more strings identifying, classifying, or describing the one or more constituent elements corresponding to the bit-screening data.

5. The method of claim 1, wherein the at least one outputted string tag comprises natural language text.

6. The method of claim 1, wherein the document data comprises metadata for identifying the document.

7. The method of claim 1, wherein determining the at least one string tag comprises:
determining one or more encoded strings based on a portion of the connection data; and
augmenting the document data to comprise the one or more encoded strings.

8. A system comprising:
one or more processors; and
memory storing computer-readable instructions that, when executed by the one or more processors, cause the one or more processors to:
receive document data corresponding to a document, wherein the document data comprises chemical structure data corresponding to a chemical structure, and the chemical structure data comprises a graphical representation of the chemical structure;
determine bit-screening data and connection data based on the chemical structure data, wherein:
the bit-screening data corresponds to one or more constituent elements of the chemical structure, and
the connection data corresponds to one or more connections between the one or more constituent elements of the chemical structure;
determine at least one string tag based on at least a portion of the bit-screening data,
wherein the at least one string tag comprises an alphanumeric value for describing the chemical structure corresponding to the chemical structure data;
determine an association of the at least one string tag with the document data;
output the at least one string tag; and
index the document data based on the at least one outputted string tag, wherein the chemical structure data corresponding to a chemical structure in the document is searchable based on correlating at least a portion of text data of a query with the indexed document data.

9. The system of claim 8, wherein the instructions, when executed by the one or more processors, further cause the one or more processors to:
augment the document data to comprise the at least one outputted string tag.

10. The system of claim 8, wherein the instructions, when executed by the one or more processors, cause the one or more processors to determine the at least one string tag at least by:
performing an atom-by-atom search or a structure-based search on the bit-screening data to identify the one or more constituent elements corresponding to the bit-screening data; and
populating the at least one string tag with one or more strings identifying, classifying, or describing the one or more constituent elements.

11. The system of claim 8, wherein the instructions, when executed by the one or more processors, cause the one or more processors to determine the at least one string tag at least by:
converting the bit-screening data into one or more strings identifying, classifying, or describing the one or more constituent elements corresponding to the bit-screening data.

12. The system of claim 8, wherein the at least one outputted string tag comprises natural language text.

13. The system of claim 8, wherein the document data comprises metadata for identifying the document.

14. The system of claim 8, wherein the instructions, when executed by the one or more processors, cause the one or more processors to determine the at least one string tag at least by:
determining one or more encoded strings based on a portion of the connection data; and
augmenting the document data based on the one or more encoded strings.

15. A non-transitory machine-readable storage medium comprising computer-readable instructions that, when executed, cause a computing device to:
receive document data corresponding to a document, wherein the document data comprises chemical structure data corresponding to a chemical structure, and the chemical structure data comprises a graphical representation of the chemical structure;
determine bit-screening data and connection data based on the chemical structure data, wherein:
the bit-screening data corresponds to one or more constituent elements of the chemical structure, and
the connection data corresponds to one or more connections between the one or more constituent elements of the chemical structure;
determine at least one string tag based on at least a portion of the bit-screening data, wherein the at least one string tag comprises an alphanumeric value for describing the chemical structure corresponding to the chemical structure data;
determine an association of the at least one string tag with the document data;
cause output of the at least one string tag for indexing the document; and
index the document data based on the at least one outputted string tag, wherein the chemical structure data corresponding to a chemical structure in the document is searchable based on correlating at least a portion of text data of a query with the indexed document data.

16. The non-transitory machine-readable storage medium of claim 15 wherein the instructions, when executed, further cause the computing device to:
augment the document data to comprise the at least one outputted string tag.

17. The non-transitory machine-readable storage medium of claim 15, wherein the instructions, when executed, cause the computing device to determine the at least one string tag at least by:
performing an atom-by-atom search or a structure-based search on the bit-screening data to identify the one or more constituent elements corresponding to the bit-screening data; and
populating the at least one string tag with one or more strings identifying, classifying, or describing the one or more constituent elements.

18. The non-transitory machine-readable storage medium of claim 15, wherein the instructions, when executed, cause the computing device to determine the at least one string tag at least by:
converting the bit-screening data into one or more strings identifying, classifying, or describing the one or more constituent elements corresponding to the bit-screening data.

19. The non-transitory machine-readable storage medium of claim 15, wherein the at least one outputted string tag comprises natural language text.

20. The non-transitory machine-readable storage medium of claim 15, wherein the document data comprises metadata for identifying the document.

\* \* \* \* \*